United States Patent [19]

Yamanishi

[11] 4,267,844
[45] May 19, 1981

[54] MEDICAL INSTRUMENT FOR DETERMINING JAUNDICE

[75] Inventor: Akio Yamanishi, Tondabayashi, Japan

[73] Assignee: Minolta Camera Kabushiki Kaisha, Osaka, Japan

[21] Appl. No.: 35,230

[22] Filed: May 2, 1979

[30] Foreign Application Priority Data

May 15, 1978 [JP] Japan .................................. 53/57867

[51] Int. Cl.³ .............................................. A61B 5/00
[52] U.S. Cl. ..................................... 128/633; 128/665
[58] Field of Search ........................ 128/633, 665–667; 356/39–41

[56] References Cited

U.S. PATENT DOCUMENTS 4,029,085  6/1977  DeWitt et al. ...................... 128/633

OTHER PUBLICATIONS

Ballowitz, L. et al., "Spectral Reflectance of the Skin", Biol. Neonate, vol. 15, pp. 348–360 (1970).
Edholm, P. "A Method for Estimating Aortic Atheromatosis", Lancet, vol. 1, Mar. 1964, pp. 535–537.

Primary Examiner—Robert W. Michell
Assistant Examiner—Francis J. Jaworski
Attorney, Agent, or Firm—Jackson, Jones & Price

[57] ABSTRACT

An electro-optical medical instrument is provided for measuring the presence of bilirubin in skin tissue. The instrument is preferably hand-held and self-contained and utilizes a source of flash light to provide sufficient energy in the desired wavelength spectrums. The medical instrument can be automatically activated at a predetermined pressure against a patient's skin to provide a pair of measurement electrical signals. These electrical signals can be processed to provide an output signal representative of the bilirubin value which can be conveniently displayed.

23 Claims, 13 Drawing Figures

MEDICAL INSTRUMENT FOR DETERMINING JAUNDICE

BACKGROUND OF THE INVENTION

1. Field of the Invention

The present invention relates to a medical instrument for examining newborn babies and more particularly to a calibrated optical-electro instrument for objectively determining the degree of jaundice in newborn babies.

2. Description of the Prior Art

The medical profession is aware of the importance of determining the existence of jaundice immediately after the birth of a baby. A large number of newborn children exhibit some degree of jaundice and frequently a jaundice test is performed as a regular routine in the delivery room. The degree of jaundice can range from a physiologically permissible level which will disappear within a short period of time after the birth to various severe degrees of jaundice, progressing to nuclear jaundice which can result in the death of a newborn or cerebral palsy as sequela even when the child is saved from death. While an accurate examination of the intensity of the jaundice condition can be determined by a measurement of the bilirubin value of the blood serum taken from newborns, it can be rather difficult or is often even unnecessary to take blood from each and every newborn for this measurement. Generally, doctors have made a visual observation of the color of the newborn's skin and then decided if there was any necessity to take a blood specimen for measurement of the bilirubin value of the blood serum.

To assist the doctors in making this visual observation the Gosset Icterometer has been developed and is employed as a screening test for deciding whether there is a need to test the bilirubin value of the blood serum. Basically, the Gosset Icterometer utilizes a plurality of standard color strips that are pressed against the skin of the baby and visually matched. Problems existed, however, due to the spectral reflection factors of the yellowish reference strips on the Icterometer, particularly under artificial illumination. Accordingly, although the prior art Icterometer has been of great assistance to the medical profession as a preliminary screening method, it frequently was necessary to rely upon the actual measurements of bilirubin in the blood serum from simply a safety point of view. Thus, quite frequently there are occasions of drawing blood from newborns that are in good health.

Of interest to the present invention is the work of Ballowitz and Avery, "Spectral Reflectance of the Skin", Biol. Neonate 15: 348–360 (1970) and U.S. Pat. No. 4,029,085. Cited of general interest are several patent disclosures relating to oximeters such as U.S. Pat. No. 3,638,640; U.S. Pat. No. 3,677,648; U.S. Pat. No. 3,814,081 and U.S. Pat. No. 3,998,550.

Accordingly, there is still a demand in the prior art to provide a safe and reliable objective test to determine the degree of jaundice in newborn babies.

SUMMARY OF THE INVENTION

An electro-optical medical instrument for determining, from an objective viewpoint, the degree, if any, of jaundice in a newborn baby is provided. A light source capable of providing a pair of wavelengths of light having approximately the same absorption coefficients with respect to hemoglobin is used in one embodiment of the present invention. Preferably, the light emitted from the light source has a sufficient quantity of light at a wavelength at or below the maximum wavelength of bilirubin absorption which is in the vicinity 455 m$\mu$. In a preferred embodiment of the present invention, the light source produces predetermined flashes of light and utilizes integration circuits and sample hold circuits between a photoelectric converting member and amplifiers. A pair of electrical signals is produced with respect to two separate wavelengths of light and these signals are processed by appropriate circuit means to provide a determination of the bilirubin value in the baby's tissue.

The embodiment of the invention that utilizes a flash source of light can further incorporate a switch designed to be activated at a certain pressure, for example, at a certain force against the baby's skin to activate the light source. Since the intensity of the flash light decays in an exponential function of time a circuit provides the capability of measuring the length of the period of time between one of the two wavelength signals reaching a predetermined level and the time when the other signal reaches the predetermined level. The period of time is a function of the bilirubin density of the hypodermic tissue.

The features of the present invention which are believed to be novel are set forth with particularity in the appended claims. The present invention, both as to its organization and manner of operation, together with further objects and advantages thereof, may best be understood by reference to the following description, taken in conjunction with the accompanying drawings.

DESCRIPTION OF THE PREFERRED EMBODIMENTS

The following description is provided to enable any person skilled in the medical field to make and use the invention and sets forth the best modes contemplated by the inventor of carrying out his invention. Various modifications, however, will remain readily apparent to those skilled in this field since the generic principles of the present invention have been defined herein specifically to provide a relatively economical and easily manufactured medical instrument for determining jaundice in newborn babies.

Figures 1, 2, 3:
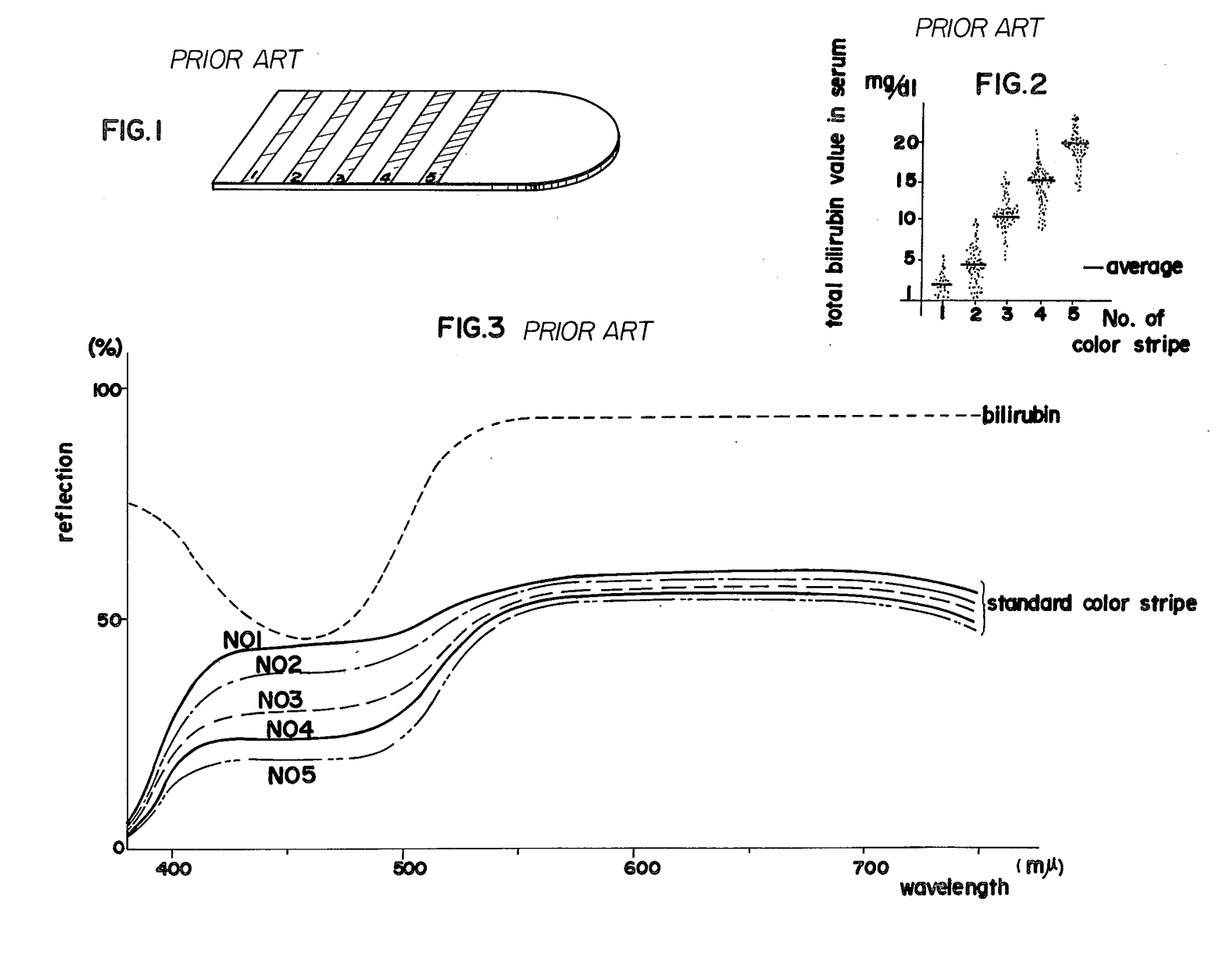
FIG. 1 is a perspective view of a Gossett Icterometer.
FIG. 2 is a graph showing the relationship between the Gosset Icterometer scale and the total bilirubin value in te blood serum.
FIG. 3 is a chart showing the spectral reflection characteristics of the referenced color strips of the Gosset Icterometer together with the spectral reflection characteristics of the bilirubin.

Referring to FIG. 1, the prior art Gosset Icterometer is disclosed in a perspective view. Basically, this device comprises a transparent base member supporting a plurality of strips with yellowish reference colors and different color tones extending across the width of the base member. These color reference strips are labeled No. 1 through No. 5 and are spaced along the longitudinal axis to permit alternative transparent portions to exist between two adjacent reference color strips. The doctor would take the icterometer and press it against the nose of a newborn child so that the flesh would be seen through the transparent strips. The underlying blood in the tissue of the nose would be scattered by the exerted pressure to reveal the original color of the skin. The doctor would then compare the color of the pressed skin with the respective yellowish reference color strips as an index and attempt to determine the closest identifying number of the yellowish reference color strips to that of the actual color of the skin.

The value obtained from the icterometer and the actual bilirubin value of the blood serum of the child were correlated as indicated on the chart in FIG. 2. This approach was practical because the unconjugated bilirubin is fat soluble and accumulates to a large degree in the hypodermal tissue which contains the greatest proportion of fat in the body of a newborn child. However, as can be determined from the graph in FIG. 3, the spectral reflection characteristics of the yellowish reference strips in the icterometer differ from the actual reflection by bilirubin and accordingly, a comparison of the skin color with the reference colors was not accurate, particularly under artificial illumination and suffered from variations relating to the subjective application of the test by either the doctor or the nurse. As a result, a doctor would utilize the icterometer test in a conservative manner to insure a sufficient safety factor in determining the degree of jaundice in a newborn child.

The embodiments of the present invention which will be subsequently described herein seek to remove the subjective determinations by individual doctors with an objective standard which will permit a more accurate determination of the condition of jaundice in a newborn child. Additionally these purposes are accomplished with an apparatus that is portable and capable of providing repetitive measurements with an immediate visual display.

Figures 4, 5, 6, 7:
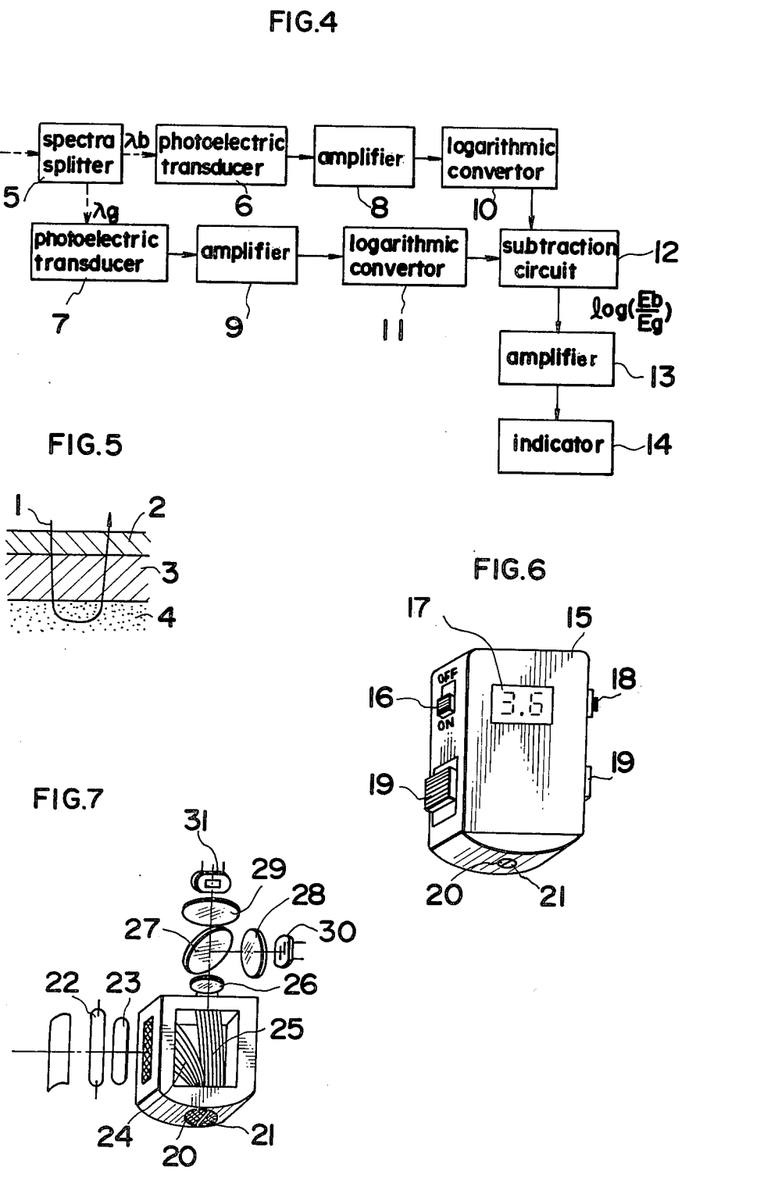
FIG. 4 is a block diagram of one preferred embodiment of the present invention.
FIG. 5 is a schematic cross-sectional view of an exemplary skin tissue.
FIG. 6 is a perspective view of another embodiment of the present invention.
FIG. 7 is an exploded perspective view of an optical system for the embodiment of FIG. 6.

Referring to FIG. 4, a first embodiment of the present invention is disclosed in a block diagram. Additionally, FIG. 5 schematically discloses a cross-sectional view of skin tissue and its effect on light. Basically light 1, emitted from a light source, finally reaches the hypodermic tissue 4 of the skin after scattering, reflection and absorption by the outer skin layer 2 and the actual or true skin tissue 3. As is well-known, the hypodermic tissue 4 contains a large amount of fat especially in newborn children so that the light 1 will have its shorter wavelengths absorbed to a larger degree due to the bilirubin content in the hypodermic fat. The light 1 reflected from the hypodermic tissue 4 again passes through the true skin 3 and outer skin 2 after additional scattering and reflection.

Although not shown in FIG. 4, it should be appreciated that a specific light source for directing light into the skin and a specific conduit for collecting light from the skin is utilized. The collected light is divided into two components by a spectroscopic means such as a spectral beam splitter 5. The splitter 5 provides at least a source of light with a wavelength $\lambda_b$ (approximately 455 m$\mu$) which permits a high absorption coefficient by the bilirubin in the skin tissue and another wavelength $\lambda_g$ (more than 500 m$\mu$) wherein the absorption coefficient of bilirubin in the skin tissue is low.

These two light components with different wavelengths are appropriately sensed by photoelectric converting means such as a photoelectric transducer 6 and 7 to produce a signal which is subsequently amplified by amplifiers 8 and 9.

The outputs $E_b$ and $E_g$ of the amplifiers 8 and 9 can be represented in the Lambert-Beer law as follows:

$$E_b = A_b \cdot I_{o\lambda b} \cdot F_{\lambda b} \cdot e^{-a_{B\lambda b} \cdot C_B \cdot d_B}$$

$$E_g = A_g \cdot I_{o\lambda g} \cdot F_{\lambda g} \cdot e^{-a_{B\lambda g} \cdot C_B \cdot d_B}$$

wherein $A_b$ and $A_g$ are the coefficients of photoelectric conversion at the wavelengths $\lambda_b$ and $\lambda_g$ (the product of the spectral transmission factor of a filter, the sensitivity of the photosensitive elements, the gain of the amplifiers, etc.);

$I_{o\lambda b}$ and $I_{o\lambda g}$ are the intensity of incident light upon the skin of the wavelengths $\lambda_b$ and $\lambda_g$;

$F_{\lambda b}$ and $F_{\lambda g}$ are the attenuation in quantity of light due to absorption, scattering and the reflection on the outer skin, the true skin and the hypodermic tissue at the wavelengths $\lambda_b$ and $\lambda_g$;

$a_{B\lambda b}$ and $a_{B\lambda g}$ are the absorption coefficients of bilirubin at the wavelengths $\lambda_b$ and $\lambda_g$;

$C_B$ is the bilirubin density; and $d_B$ is the equivalent light path length of bilirubin.

The resultant outputs $E_b$ and $E_g$ of the amplifiers 8 and 9 are then subject to logarithm conversion by logarithm converters 10 and 11 and subtraction by a subtractor circuit 12 in order to obtain ln $(E_b/E_g)$. If the coefficients $A_b$ and $A_g$ are adjusted to assure $A_b \cdot I_{o\lambda b} \cdot F_{\lambda b} = A_g \cdot I_{o\lambda g} \cdot F_{\lambda g}$ (this can in fact be accomplished by adjusting the gains of the amplifiers 6 and 7), then:

$$\ln (E_b/E_g) = (a_{B\lambda g} - a_{B\lambda b}) \cdot C_B \cdot d_B$$

Since $a_{B\lambda b}$ and $a_{B\lambda g}$ are known values and $d_B$ assumes substantially a fixed value inherent to a specific measuring point, e.g., the forehead, the bilirubin density in the hypodermic tissue can accordingly be evaluated through ln $(E_b/E_g)$. The bilirubin density is appropriately displayed on an indicator or display means 14 via an amplifier 13.

It should be noted that human blood vessels are widely distributed in the true skin 3 of FIG. 5 so that $E_b$ and $E_g$ may be under the influence of absorption by the blood. To eliminate such influences of absorption by the blood, the light outlet and light intake are disposed very close to each other and the measurements are conducted under a condition such that the blood is scattered out from the blood vessels in the true skin to reduce the influences of absorption by blood to a minimum. This can be accomplished by pressing strongly against the skin.

An electronic flash tube that can be appropriately timed for emission of light, as subsequently described in FIGS. 6 and 7, can be used with the embodiment of FIG. 4.

In addition, should the wavelengths $\lambda_b$ and $\lambda_g$ be selected from within ranges of wavelengths corresponding to blue and green light respectively, the absorption coefficients would be approximately equal to each other with respect to hemoglobin so that the ratio of $E_b$ to $E_g$ and hence the intended value of ln $(E_b/E_g)$ are free from any influences of the amount of blood. Therefore, even when blood is incompletely removed from the tissue, it is still possible to minimize an error in measurement.

The foregoing description is true when employing a source of constant light such as a tungsten lamp. The quantity of light emission is, however, critical since the maximum wavelength of bilirubin absorption is in the vicinity of 455 m$\mu$ and the energy emitted from the tungsten lamp is relatively weak in the short wavelength range whereas the sensitivity of a silicon photocell is considerably low for short wavelength light.

Therefore, in a case where a light source such as the tungsten lamp or the like is employed, it is necessary to insure the release of a significant quantity of light. This, however, results unavoidably in a large-sized lamp device and great inconvenience in measuring newborns in bed or the nursing room. Accordingly, the present invention finds it desirable to use an electronic flash tube such as a xenon flash tube which is of a hand-held size and emits a satisfactory quantity of light in the desired range per unit of time.

With this preferred embodiment of the invention, the light source produces flashes of light and further requires integration circuits and sample hold circuits between the photoelectric converting means 6 and 7 and the amplifiers 8 and 9 respectively of the embodiment of FIG. 4.

In FIGS. 6 through 9, there is illustrated another embodiment of the present invention. FIG. 6 shows, in a perspective view, an instrument accommodated within a housing 15 of a pocket size, which includes a power switch 16, a digital display panel 17 and a reset button 18. A holder 19 extends from both sides of the housing 15 and is movable upward and downward relative to the housing 15 and is normally biased upwardly. A light emitter or outlet is labeled 20 and the light intake is labeled 21.

FIG. 7 is an exploded perspective view of an optical system mounted within the housing 15 of the above embodiment. Light released from the Xenon flash tube 22 is guided to the light outlet 20 via a heat absorbing filter 23 and light source fiber guides 24 so as to impinge upon the skin at a specific measuring point. The return light reaches the light intake 21 after suffering from intense absorption in the blue light wavelength range due to the bilirubin contained within the hypodermic fat and then is transmitted to a condenser lens 26 via fiber optic guides 24. Such resulting light is divided into blue and green light components through a dichroic mirror 27 and is received at light responsive elements 30 and 31 after passing through a blue filter 28 and a green filter 29, respectively.

Prior to any measurements, the power switch 16 in FIG. 6 is turned on, the reset button 18 is depressed and the light outlet 20 and the light intake 21 are pressed against the forehead of newborns while being grasped by means of the holder 19. At this moment, the holder 19 is shifted downward with respect to the housing 15 against a predetermined biasing force. When the biasing force, which is equal to the pressure of forcing the light outlet and intake 20 and 21 against the skin, becomes a predetermined value of pressure, namely, when the holder 19 is shifted a predetermined distance with respect to the housing 15, a trigger switch is automatically closed for activation of the xenon flash tube 22 so that tube 22 releases a flash of light for measuring purposes. Thus, the force of pressuring the skin provides timing means for determining the firing of the flash. This insures that the pressing force for scattering out blood is unchanged for each measurement and further avoids any fear of applying too much pressure to newborns. Therefore, the above embodiment is suitable for prompt sequential measurements. Since the light outlet 20 and the light intake 21 pressed against the skin, the ambient illumination light is prevented from entering into the light intake 21.

When it is desired to conduct measurements at a different physical point such as the ear lobe, it may be sandwiched on both sides by the light outlet and the light intake. In this case, the measurement device is of a light transmission type.

Figure 8:
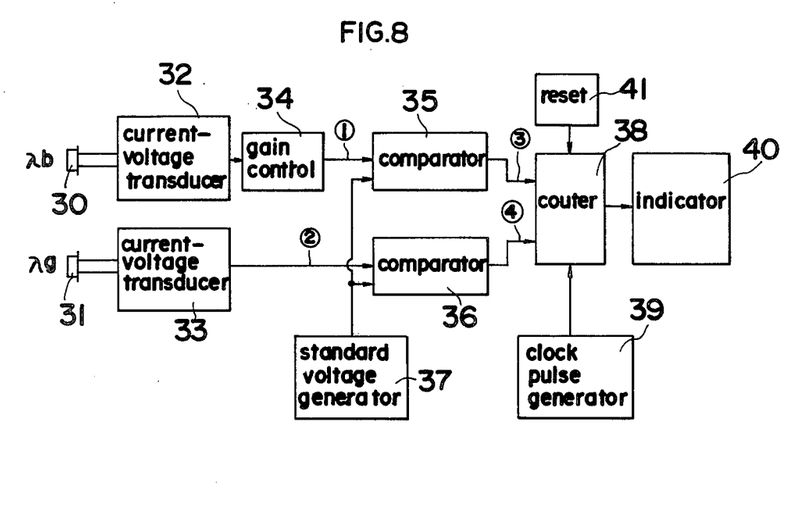
FIG. 8 is a block diagram of the electrical circuit in the embodiment of FIG. 6.

FIG. 8 shows a block diagram of the signal processing from the light receiving elements 30 and 31 to the indicator 40 for the FIG. 6 embodiment. The construction disclosed in FIG. 8 incorporates the invention described in my copending U.S. patent application Ser. No. 16,561 filed Mar. 1, 1979 entitled "APPARATUS FOR OPTICALLY MEASURING A PROPERTY OF AN OBJECT" assigned to the same assignee as this application.

The light source is provided by a source of flash light such as an electronic flash tube of which the quantity of light emitted attenuates as an exponential function of the passage of time. A value proportional to the logarithm of a ratio of the outputs of the light receiving elements 30 and 31 is evaluated by measuring a period of time between two different points in time; one point where the output of the light responsive element 30 reaches a predetermined level due to light attenuation and the other point where the output of the light responsive element 31 reaches the predetermined level. The output current of the light responsive element 30 is converted via a current-to-voltage converter 32 into an output voltage which in turn is adjusted via again adjustment circuit 34 at the node ① of FIG. 8. The output current of the light responsive element 31, on the other hand, is converted into a corresponding output voltage via a current-to-voltage converter 33 at the node ② .

Since the manner wherein the quantity of light emission from the flash tube attenuates is according to an exponential function of time, the output voltages at the nodes ① and ② assume the following values at a specific point, t, in time as long as a reference point in time is in agreement with the emission rising edge and the quantity of light emission begins to attenuate in the form of logarithmic function at $t_o$ (wherein $\tau$ is the time constant):

$$V_b = V_{ob} \cdot e^{-\frac{t-t_o}{\tau}} \tag{1}$$

-continued $$V_r = V_{ob} \cdot e^{-\frac{t-t_0}{\tau}} \quad (2)$$

In the above defined formulas, $$V_{ob} = A_b \cdot I_{o\lambda b} \cdot F_{\lambda b} \cdot e^{-a_{B\lambda b} \cdot C_B \cdot d_B} \quad (3)$$

$$V_{og} = A_g \lambda \cdot I_{o\lambda g} \cdot F_{\lambda g} \cdot e^{-a_{B\lambda g} \cdot C_B \cdot d} \quad (4)$$

Through gain adjustment, the following relationship is achieved:

$$A_{g\lambda} \cdot I_{o\lambda g} \cdot F_{\lambda g} = A_b \cdot I_{o\lambda b} \cdot F_{\lambda b}$$

The outputs at the nodes ① and ② are applied to comparators 35 and 36 for comparison with a reference voltage from a reference voltage generator 37. The output voltage of the comparator 35 (or 36) at the nodes ③ (or ④) is high when the voltages at the nodes ① (or ②) is higher than the reference voltage. Otherwise the output voltage is low. The voltage waveforms appearing at the nodes ①, ②, ③ and ④ are depicted in a timing diagram shown in FIG. 9.

Figure 9:
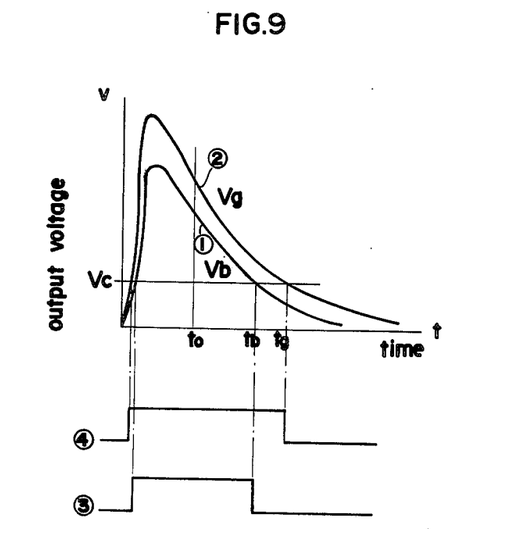
FIG. 9 is a timing diagram of voltage versus time length signals of the embodiment of FIG. 6.

If $V_c$ is the reference voltage and $t_b$ and $t_g$ are the points in time wherein the voltages at the nodes ① and ② become equal to $V_c$, then $$V_c = V_{ob} \cdot e^{-\frac{t_b - t_0}{\tau}} \quad (5)$$

$$V_c = V_{og} \cdot e^{-\frac{t_g - t_0}{\tau}} \quad (6)$$

From the formulas (5) and (6), $$\frac{V_{ob}}{V_{og}} = e^{\frac{t_g - t_b}{\tau}} \quad (7)$$

Therefore, $$t_g - t_b = \tau \cdot \ln(V_{og}/V_{ob}) \quad (8)$$

Considering formulas (3) and (4), the formula (8) can be rewritten as follows:

$$t_g - t_b = \tau \cdot (a_{B\lambda b} - a_{B\lambda g}) C_B \cdot d_B \quad (9)$$

In FIG. 8, a counter 38 starts counting pulses from a clock pulse generator 39 at the point $t_b$ in time and discontinues counting at point $t_g$ in time.

As a result, the number of pulses counted is proportional to $(t_g - t_b)$ and a value proportional to the value given in the formula (9) can be evaluated. Since $\tau$, $a_{B\lambda b}$ and $a_{B\lambda g}$ are already known and $d_B$ is substantially identical if measuring points, e.g., foreheads, are identical it is thus possible to evaluate the value proportional to the bilirubin density $C_B$ of the hypodermic tissue. To evaluate the value directly indicative of $C_B$, the cycle of the clock pulses should be properly selected. A conventional means 41 is provided for resetting the count of the counter to zero.

Considering the situation where the reference voltages $V_{cg}$ and $V_{cb}$ of the comparators 35 and 36 are different, then, $$V_{cb} = V_{ob} e^{-\frac{t_b - t_0}{\tau}} \quad (10)$$

$$V_{cg} = V_{og} e^{-\frac{t_g - t_0}{\tau}} \quad (11)$$

In the same manner as obtaining formula (9), the following formula is obtained from formulas (10) and (11):

$$t_g - t_b = \tau \cdot \ln \frac{V_{og} \cdot V_{cb}}{V_{ob} \cdot V_{cg}} \quad (12)$$

$$= \tau \cdot \left\{ \ln \frac{A_g \cdot I_{o\lambda g} \cdot F_{\lambda g} \cdot V_{cb}}{A_b \cdot I_{o\lambda b} \cdot F_{\lambda b} \cdot V_{cg}} + (a_{B\lambda b} - a_{B\lambda g}) \cdot C_B \cdot d_B \right\}$$

If the following relationship exists in the above formula, $$A_g \cdot I_{o\lambda g} \cdot E_{\lambda g} \cdot V_{cb} = A_b \cdot I_{o\lambda b} \cdot E_{\lambda b} \cdot V_{cg} \quad (13)$$

then $$t_g - t_b = \tau \cdot (a_{B\lambda b} - a_{B\lambda g}) \cdot C_B \cdot d_B \quad (14)$$

The formula (14) is identical with the above defined formula (9). When the relationship as indicated by formula (13) exists in formula (12), $(t_g - t_b)$ should be zero with $C_B = 0$. This implies conversely that the relationship as set forth in formula (13) can be fulfilled by adjusting the gain so as to make $(t_g - T_b) = 0$ when $C_B = 0$.

It is, therefore, not necessarily required that a discrete reference voltage generator be provided to produce $V_c$ as the reference voltage. The comparators 35 and 36 can be a pair of known Schmitt trigger circuits for simplicity of circuit construction, which have $V_{cg}$ and $V_{cb}$ of different reference levels, respectively.

Figure 10:
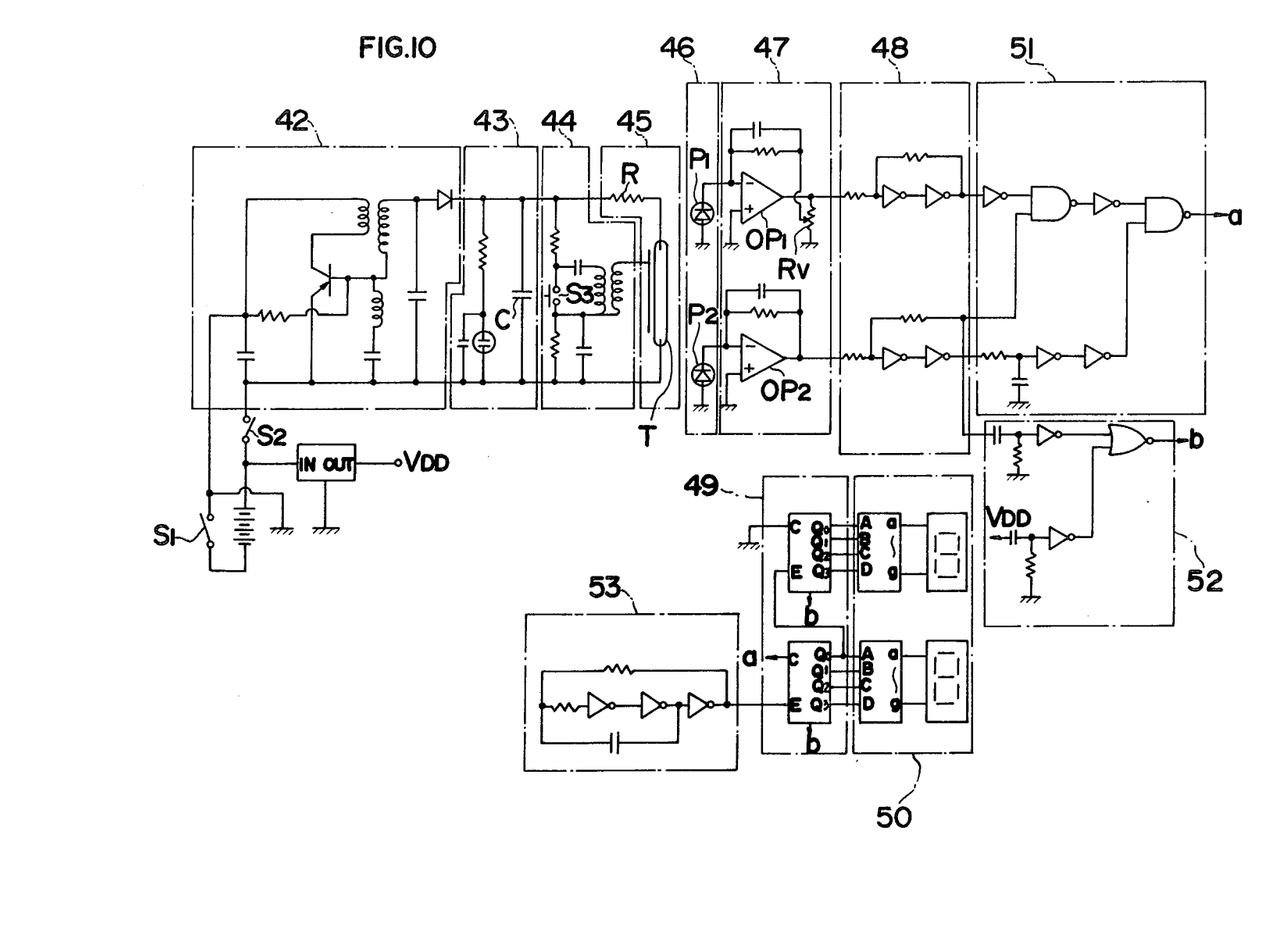
FIG. 10 is a circuit diagram of still another embodiment of the present invention.

FIG. 10 discloses still another embodiment of the present invention constructed pursuant to the teachings of the embodiments of FIGS. 6 through 9. This embodiment includes a main switch $S_1$ for supplying a measurement and display system with power from $V_{DD}$ and enabling a light source system ready for power supply, and a light source switch $S_2$. When the switch $S_2$ is closed, a main capacitor C within a charging circuit 43 is charged from a high voltage generator 42 of a well-known direct current to direct current (D—D) converter construction. Provided that a trigger switch, $S_3$, in a trigger circuit 44 is closed at the beginning of the measurements, a xenon flash tube T in a light source section 45 consumes the charge accumulated on the main capacitor C for light emission. A resistor R is provided in the light source section for increasing the time constant as to the attenuation of the quantity of light.

Through reflection from the skin tissue of newborns, the light from the xenon flash tube T is incident upon a blue light responsive silicon photocell $P_1$ and a green light responsive silicon photocell $P_2$ within a light receiving section 46.

The output of silicon photocells, $P_1$ and $P_2$, are connected respectively to amplifiers within current-to-voltage converters 47. Each of the amplifiers can be implemented by a well-known operational amplifier $OP_1$ and $OP_2$. A potentiometer $R_v$ is further provided for gain adjustment. A pair of Schmitt trigger circuits in block 48 are connected to the outputs of the amplifiers to provide outputs which are inverted according to the output levels of the amplifiers.

Two 4-bit counters 49 are provided in the order of units and tens of units and the contents are displayed via a display circuit 50 comprising a decoder driver and a seven-segment display element. The output pulses from a clock pulse generator 53 are connected to the input E of the counter 49 in the order of units during the period of time where its gate terminal is at low level.

A timing circuit 51 comprises a combination of conventional logic circuits and delay circuits, and gates the gate terminal a of the counter 49. The output terminal a thereof is low during a period between two points in time; one point, wherein the output of one of the Schmitt trigger circuits changes from high to low due to attenuation of the output of the blue light responsive silicon photocell $P_1$ and the other point wherein the output of the other Schmitt trigger circuit changes from high to low due to that of the green light responsive silicon photocell $P_2$.

A reset circuit 52 is adapted to receive the output of the Schmitt trigger circuit changeable in response to the output of the green light responsive silicon photocell $P_2$ and a signal developed when the main switch $S_1$ is closed. Upon closure of the main switch $S_1$, the reset circuit 52 receives the signal at $V_{DD}$ and provides a reset signal at the output b. The reset signal is received at a reset terminal b of the counter 49 to reset the count to zero. On the other hand, when the xenon flash tube releases light and the output of the green light responsive silicon photocell exceeds the value of a reference potential, the output of the Schmitt trigger circuit changes from low to high so that the reset circuit provides the reset signal at the output terminal b, again resetting the count of the counter 49 to zero. Thus, before the output of the Schmitt trigger changes from high to low to initiate the counting operation due to attenuation of the output of the blue light responsive silicon photocell, the previous count of the counter 49 is automatically reset to zero and ready for a new measurement.

The above embodiment is suitable for prompt sequential measurements since the results of the previous measurement are reset automatically at the beginning of a new measurement without any particular reset operation. It should also be noted that the present invention provides a portable electrooptical medical instrument that can be held by hand and is self-contained.

Figure 11:
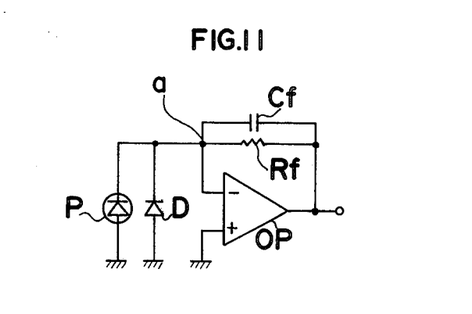
FIG. 11 is a partial circuit diagram of a modification to the embodiment of FIG. 10.

In FIG. 11, there is illustrated a further improvement in the amplifier utilized within the current-to-voltage converter 47 of the embodiment of FIG. 10, wherein a diode D is connected to the input of the operational amplifier OP in parallel with the silicon photocell P.

The embodiment of FIG. 10, utilizing attenuation of the output of the amplifier operates, in principle, successfully even when the peak value of the output of the silicon photocell, P, is so high as to saturate the amplifier and the output of the amplifier does not fully follow transitions in the output of the silicon photocell. It is enough for the amplifier to follow transitions in the output of the silicon photocell in the output attenuation region necessary for measurements.

As a matter of fact, however, if the amplifier is in a saturated condition, then the node a of FIG. 11, provided that diode D is not added, will not be in the imaginary ground condition so that the potential falls and excessive charge is accumulated on a phase-compensating capacitor Cf within the amplifier.

Figure 12:
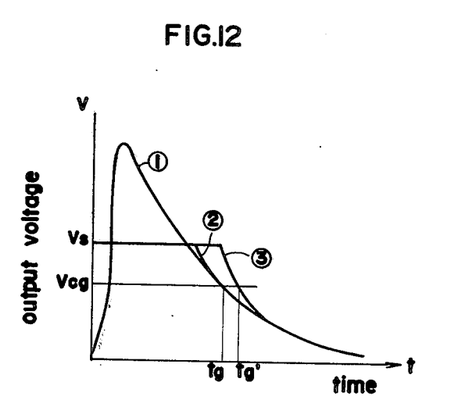
FIG. 12 is a timing diagram relating to the embodiment of FIG. 10.

The curve ① in FIG. 12 shows variations in the output of the amplifier when the power supply voltage to the amplifier is high enough not to saturate the amplifier, whereas the curve ③ depicts variations in the output of the amplifier caused by the influences of the charge accumulated on the capacitor Cf in case that amplifier is saturated at $V_s$. As a consequence, the point $t_g$, wherein the reference potential $V_{cg}$ is reached is shifted to $t_g'$.

However, in a case where a diode D is connected as indicated in FIG. 11, the forward current is shunted through the diode D after the output voltage is saturated so that the fall of potential at the node, a, is prevented and the output waveform of the amplifier approaches the curve 1 as is obvious from curve ② in FIG. 12. A high degree of accuracy is, thus, assured even when the output voltage is saturated.

Figure 13:
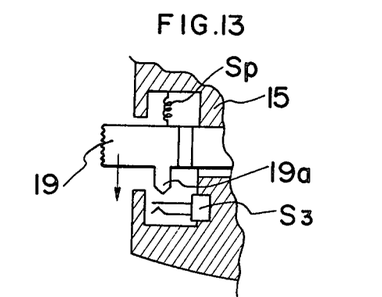
FIG. 13 is a cross-sectional view of a switching mechanism.

FIG. 13 shows a schematic connection between the trigger switch $S_3$ in FIG. 10 and the construction in FIG. 6. Holder 19, which is upward and downward slidable relative to the housing 15, is normally biased toward the upper side of the housing 15 by spring $S_p$. If the housing 15, held by the holder 19 is pressed against the skin of a newborn baby, holder 19 will be moved against the force of spring $S_p$, toward the direction of the arrow relative to the housing 15, with the lower side of the housing 15 kept in contact with the skin. When the holder 19 is shifted a predetermined value relative to the housing 15, projection 19a pushes a pair of contacts forming switch $S_3$ to a closed position. Thus, switch $S_3$ is always closed when the pressure of the lower side of the housing 15 on the skin reaches a predetermined value for actuating the flash tube T of FIG. 10 to emit a measurement flash light source.

As stated above, the present invention provides a medical instrument which performs measurements accurately, irrespective of differences in the surrounding illumination light and different operators assure a high degree of reliability in comparison with the prior art screening method. In addition, the present invention both permits an early check of jaundice which may endanger the life of newborns, while eliminating the need to draw blood from newborns in good health.

While the above embodiments have been disclosed as the best mode presently contemplated by the inventor it should be realized that these examples should not be interpreted as limiting, because artisans skilled in this field, once given the present teachings, can vary from these specific embodiments. Accordingly, the scope of the present invention should be determined solely from the following claims in which

I claim:

1. A medical instrument for determining the existence and degree of jaundice comprising:
    light source means including means for producing a flash of light containing at least two separate wavelengths;
    means for receiving light from the light source means after contact with living tissue of a person and producing a pair of electrical signals from a pair of separate wavelengths of light;
    means for automatically activating said light source means at a predetermined pressure between said medical instrument and said living tissue, and
    means for processing the pair of electrical signals to determine the bilirubin value in the tissue.

2. The invention of claim 1, wherein said light source means includes a light exit member and said light receiving means includes a light entrance member, said light exit and light entrance being configured for contact with the skin of the person.

3. The invention of claim 2, wherein said means for automatically activating includes a switch assembly for actuating said flash light producing means to emit a flash of light and means for operating said switch assembly when the pressure of the light exit and light entrance members against the skin of the person reaches a predetermined value.

4. The invention of claim 3 further comprising a supporting member positioning said light exit and light entrance members adjacent each other, and a base portion movable relatively to said supporting member, wherein said operating means operates said switch assembly after a predetermined displacement of said movable base portion relative to said supporting member is achieved.

5. The invention of claim 4, wherein the intensity of the flash light produced by said flash light producing means decays in an exponential function of time and each of said pair of electrical signals of said light receiving means changes in response to the change in intensity of received light, wherein said processing means further includes means for measuring the length of a time period between the time when one of the electrical signals reaches a predetermined level caused by the decay of intensity of said flash light and the time when the other of the electrical signals reaches a predetermined level caused by the decay of intensity of said flash light.

6. The invention of claim 5 further comprising means for resetting the measuring means in response to a measurement of the rise of one of the signals electrical values caused by the rise of said flash light.

7. The invention of claim 5 wherein said means for receiving light produces a first electrical signal corresponding to approximately 455 m$\mu$ and a second electrical signals corresponding to a wavelength greater than 500 m$\mu$.

8. A medical instrument for determining the existence and degree of jaundice comprising:
 a source of light for producing at least two separate wavelengths;
 means for directing the light into skin tissue;
 means for receiving light subsequent to contact with the skin tissue and producing a pair of electrical signals corresponding to the wavelengths;
 timing means for generating the production of the electrical signals at a predetermined pressure between the medical instrument and the skin tissue, and
 means for processing the electrical signals to provide an output signal representative of the bilirubin value in the skin tissue.

9. The invention of claim 8 wherein the source of light includes means for producing a flash of light at the predetermined pressure.

10. The invention of claim 11 wherein the processing means further includes timing means for measuring the electrical signals at predetermined values to provide a time differential proportional to the bilirubin value in the skin tissue.

11. The invention of claim 9, wherein the intensity of the flash light produced by the flash light producing means decays in an exponential function of time and each of the pair of electrical signals of light receiving means changes in response to the change in intensity of received light and the processing means further includes means for measuring the length of a time period between the time when one of the electrical signals reaches a predetermined level caused by the decay of intensity of the flash light and the time when the other of the electrical signals reaches a predetermined level caused by the decay of intensity of the flash light.

12. The invention of claim 11 further comprising means for resetting the measuring means in response to a measurement of the rise of one of the signals electrical values caused by the rise of the flash light.

13. The invention of claim 9 wherein the means for processing is electrically performed in accordance with the following equation;

$$t_g - t_b = \tau \cdot (a_{B\lambda b} - a_{B\lambda g}) C_B \cdot d_B$$

wherein,
 $C_B$ is the bilirubin concentration in the skin tissue;
 $d_B$ is the equivalent light path length of bilirubin;
 $a_{B\lambda g}$ and $a_{B\lambda b}$ are the absorption coefficients of bilirubin at the wavelengths $\lambda_g$ and $\lambda_b$ respectively, and
 $t_g$ and $t_b$ are the times measured when the decaying output value of the electrical signals produced by the flash of light reach a predetermined level for respectively $\lambda_g$ and $\lambda_b$ wavelengths of light.

14. The invention of claim 9 wherein the timing means includes a housing member for supporting the means for directing the flash light into skin tissue and a resilient switch assembly capable of being grasped by an operator and relatively moved to the housing member to generate the predetermined pressure against the skin tissue.

15. A medical instrument for determining the existence and degree of jaundice comprising:
 light source means for producing a flash of light containing at least two separate wavelengths including a light exit member and a switch assembly for actuating said flash light producing means to emit a flash of light;
 means for receiving light from the light source means after contact with living tissue of a person and producing a pair of electrical signals from a pair of separate wavelengths of light including a light entrance member, said light exit and light entrance members being configured for contact with the skin of the person;
 means for activating said switch assembly when the pressure of the light exit and light entrance members against the skin of the person reaches a predetermined value, and
 means for processing the pair of electrical signals to determine the bilirubin value in the tissue.

16. The invention of claim 15 further comprising a supporting member positioning said light exit and light entrance members adjacent each other, and a base portion movable relatively to said supporting member, wherein said means for activating operates said switch assembly after a predetermined displacement of said movable base portion relative to said supporting member is achieved.

17. The invention of claim 16 wherein the intensity of the flash light produced by said flash light producing means decays in an exponential function of time and each of said pair of electrical signals of said light receiving means changes in response to the change in intensity of received light, wherein said processing means further includes means for measuring the length of a time period between the time when one of the electrical signals reaches a predetermined level caused by the decay of intensity of said flash light and the time when the other of the electrical signals reaches a predetermined level caused by the decay in intensity of said flash light.

18. The invention of claim 17 further comprising means for resetting the measuring means in response to a measurement of the rise of one of the signals electrical values caused by the rise of said flash light.

19. The invention of claim 17 wherein said means for receiving light produces a first electrical signal corresponding to approximately 455 mµ.

20. A medical instrument for determining the existence and degree of jaundice comprising:
   light source means including means for producing a flash of light, whose intensity decays in an exponential function of time, containing at least two separate wavelengths of light;
   means for receiving light from the light source means after contact with living tissue of a person and producing a pair of electrical signals from a pair of separate wavelengths of light, each electrical signal of the light receiving means changes in response to the change in intensity of received light, and
   means for processing the pair of electrical signals to determine the bilirubin value in the tissue including means for measuring the length of a time period between the time when one of the electrical signals reaches a predetermined level caused by the decay of intensity of the flash light and the time when the other of the electrical signals reaches a predetermined level caused by the decay of intensity of the flash light.

21. The invention of claim 20 further comprising means for resetting the measuring means in response to a measurement of the rise of one of the signals electrical values caused by the rise of the flash light.

22. The invention of claim 20 wherein the means for processing is electrically performed in accordance with the following equation:

$$t_g - t_b = \tau \cdot (a_{B\lambda_b} - a_{B\lambda_g}) C_B \cdot d_B$$

wherein,
   $C_B$ is the bilirubin concentration in the skin tissue;
   $d_B$ is the equivalent light path length of bilirubin;
   $a_{B\lambda_g}$ and $a_{B\lambda_b}$ are the absorption coefficients of bilirubin at the wavelengths $\lambda_g$ and $\lambda_b$ respectively; and
   $t_g$ and $t_b$ are the times measured when the decaying output value of the electrical signals produced by the flash of light reach a predetermined level for respectively $\lambda_g$ and $\lambda_b$ wavelengths of light.

23. The invention of claim 22 further comprising means for automatically activating said light source means at a predetermined pressure between said medical instrument and said living tissue.

* * * * *